United States Patent
Hiltl

(10) Patent No.: US 9,078,641 B2
(45) Date of Patent: Jul. 14, 2015

(54) DEVICE FOR RECEIVING OF DISPOSABLE ITEMS FOR AN OPERATING ROOM

(75) Inventor: Christoph Hiltl, Singen (DE)

(73) Assignee: KARL STORZ GMBH & CO. KG (DE)

( * ) Notice: Subject to any disclaimer, the term of this patent is extended or adjusted under 35 U.S.C. 154(b) by 879 days.

(21) Appl. No.: 12/855,233

(22) Filed: Aug. 12, 2010

(65) Prior Publication Data

US 2011/0036738 A1    Feb. 17, 2011

(30) Foreign Application Priority Data

Aug. 14, 2009    (DE) .......................... 10 2009 037 315

(51) Int. Cl.
*G06F 17/00* (2006.01)
*A61B 19/02* (2006.01)
*B65F 1/00* (2006.01)
*B65F 1/14* (2006.01)
*A61B 19/00* (2006.01)

(52) U.S. Cl.
CPC ........... *A61B 19/0287* (2013.01); *B65F 1/0046* (2013.01); *B65F 1/1484* (2013.01); *B65F 1/1638* (2013.01); *A61B 2019/448* (2013.01); *A61B 2019/4826* (2013.01); *B65F 2001/008* (2013.01); *B65F 2210/112* (2013.01); *B65F 2210/1123* (2013.01); *B65F 2210/128* (2013.01); *B65F 2210/144* (2013.01); *B65F 2210/182* (2013.01); *B65F 2210/184* (2013.01)

(58) Field of Classification Search
USPC ................................................. 235/375, 385
See application file for complete search history.

(56) References Cited

U.S. PATENT DOCUMENTS

| | | | |
|---|---|---|---|
| 6,759,959 B2 * | 7/2004 | Wildman | 340/572.1 |
| 2002/0196150 A1 | 12/2002 | Wildman | |
| 2004/0245134 A1 | 12/2004 | Alcouloumre et al. | |
| 2006/0212307 A1 * | 9/2006 | Mallett et al. | 705/1 |
| 2007/0080223 A1 | 4/2007 | Japuntich | |
| 2008/0139866 A1 | 6/2008 | Fisher et al. | |
| 2008/0195247 A1 | 8/2008 | Mallett et al. | |

FOREIGN PATENT DOCUMENTS

| | | |
|---|---|---|
| DE | 2146823 A1 | 3/1973 |
| DE | 19612602 A1 | 10/1997 |
| WO | 2005029286 A2 | 3/2005 |
| WO | 2009030877 A1 | 3/2009 |

OTHER PUBLICATIONS

European Search Report; Application No. EP10008074; Nov. 17, 2010; 4 pages.

* cited by examiner

*Primary Examiner* — Rafferty Kelly
(74) *Attorney, Agent, or Firm* — Whitmyer IP Group LLC

(57) ABSTRACT

A system for receiving of disposable items in an operating room, where the objects that are to be disposed of and which are equipped with a data carrier are automatically acquired and electronically registered in databases. The data carrier on the objects can be RFID tags or a barcode. The data read out are used in particular to individually recognize the type, quantity, and value of an object and to be able to document and display the type, quantity, and value of an object by using an electronic inventory and value determination process.

19 Claims, 2 Drawing Sheets

DEVICE FOR RECEIVING OF DISPOSABLE ITEMS FOR AN OPERATING ROOM

CROSS-REFERENCE TO RELATED APPLICATIONS

The present application claims priority of German patent application No. 10 2009 037 315.2 filed on Aug. 14, 2009, the content of which is incorporated herein by reference.

FIELD OF THE INVENTION

The present invention relates to a device for receiving of disposable items.

BACKGROUND OF THE INVENTION

Disposal items include, in particular, surgical instruments, expendable medical items, and sterile packagings, that is, containers in which a sterile material remains until its immediate use.

A device for receiving of disposable items for an operating room is disclosed in patent DE-OS 2146823.

Surgical instruments and sterile materials such as swabs and surgical cloths required in operations, after use, are deposited directly into such a disposal container or are placed in other receptacles such as sieve baskets. For medical documentation it is then customary to document the used articles in an OR documentation list. This task is performed entirely manually. It is very laborious and time-consuming, and therefore requires highly specialized nursing staff who are familiar with the individual instruments, expendable materials, and sterile supplies and can perform the manual documentation without transmission errors.

The complexity of handling sterile materials, in the meantime, requires a sterile materials management that is capable of rapidly capturing and mastering all procedures connected with sterility in a hospital. The principle of identification and retraceability is just one of the essential tasks.

It is the object of the present invention to perfect a device for receiving of disposable items in such a way that improved documentation becomes possible.

SUMMARY OF THE INVENTION

This object is achieved by means of a device for receiving of disposable items, with the traits of claim 1. The subsidiary claims indicate elaborations of the invention.

The inventive device includes a container equipped with an opening and an identification unit, which is positioned in the area of the container's opening.

On the basis of the inventive device it is possible securely to acquire an object equipped with one or more data carriers and to read out data from the data carrier when said carrier is subjected to the detection area of the identification unit. The primary advantages that result from this are: time saving in acquiring the objects, fewer errors in documentation, and the fact that the device can be used easily and intuitively and consequently requires no specialized training of personnel.

The inventive identification unit advantageously comprises at least one reader head, which shows a continuing detection area that completely covers the container's opening and acquires it while extending horizontally in particular, preferably parallel to the surface of the container's opening, and corresponds to the profile of the perimeter of the opening of the container. The area of detection here corresponds in particular to the container's opening. This ensures that every object that is equipped with a data carrier and is inserted into the container is reliably acquired and the data of the data carrier can be correspondingly read out. In addition, thanks to the selected configuration of the identification unit, the possibility of erroneous detection is also excluded, that is, the risk of unwittingly capturing objects that are found outside the container and are conducted along the identification unit in close proximity to it. Thus, thanks to the identification unit, one can ensure the acquisition exclusively of the objects that in fact are to be disposed of, and in a preferred embodiment, in addition, they are also identified. In addition to the acquired data, in addition and alternatively, other data can be documented for the identified objects and subjected to an additional evaluation.

In another preferred embodiment of the inventive device, the identification unit comprises two or more reader heads. These are preferably positioned and oriented in such a way that the respective detection areas of the mutually adjoining and/or facing reader heads overlap and together form a continuous detection area. Such a configuration has the advantage of ensuring the reliable acquisition of objects equipped with data carriers. According to the invention, a secure record is nevertheless achieved, in particular with objects whose data carrier is found in a non-readable position for an individual reader head and/or objects that comprise screening components that disturb the process.

One or more of the reader heads of the inventive device can preferably be configured as barcode scanners and/or RFID reader devices. These devices are appropriate for their ability to read out information without contact from data carriers, such as barcode labels or RFID data carriers—also known as RFID tags. This occurs largely independently of the soiling of the objects that are to be removed. Additional advantages of RFID data carriers and RFID laser devices consist in the higher storage capacity, and greater speed of reading and identification in comparison with other conventional data carriers and related reader devices such as barcode systems. Data can also be acquired directly and precisely. The data, in particular, can be taken from the data group product name, article designation, lot number, usability/expiration date, or series number.

In addition, such reader devices constitute standardized components with a high capturing precision, thanks to which it is possible to produce an economical device. The advantage of a barcode or barcode scanner system resides, in particular, in the fact this technology in the field of automatic recognition systems has matured and has already been widely used in many fields for several years. The objects that are to be removed can also be labeled in simple and reliable manner and thus can be especially simply acquired and subjected to documentation.

By means of the reader heads, which preferably are configured as barcode scanners and/or RFID reader devices, data can be read out as an object to be removed from its data carrier and later can be documented. In the framework of an additional evaluation, these data can then be complemented with additional data, in particular from a database, and correspondingly subjected to an additional evaluation and documentation. This can lead, for instance, to material flow information. In the framework of an optional identification by means of the identification unit, it is possible on the basis of the acquired data also to make an identification by comparison with previously stored material data, where these data are filed in a remote database or in a database associated with the identification unit. In the latter case the database is updated regularly or, depending on the situation, on the basis of a remote database, in particular in the hospital's central computer. As a result, a very current and reliable documentation can be maintained.

An additional configuration of the inventive device provides that the identification unit is connected by means of a communication link with an evaluation unit that is remote from it, and the data read out by the identification unit are transmitted to the evaluation unit preferably over this communication link. To achieve a local data transfer, the identification unit in this case can be physically connected with the evaluation unit by a data cable. The use of a data cable, however, involves the risk of stumbling over the cable or of unintended severing of the cable from the identification unit and/or the evaluation unit by an impact or pulling motion.

Alternatively and preferably, the data transfer should occur wirelessly, for instance by means of an IR or Bluetooth connection, which proves especially useful with frequent changes of location for the inventive device.

Transmission of data can proceed in real time, that is, during an ongoing identification and the reading of an object directed to a reader head and equipped with a data carrier, without substantial delay. Consequently it is possible in advantageous manner to dispense with particular data storage systems for intermediate storage within the identification unit and to keep said unit correspondingly small and economical to produce.

Alternatively, it is also possible in the area of the identification unit or of the communication link to produce data storage devices by which the data can first be stored and then, or at least with a time delay, read and forwarded.

It is also possible to conduct a simple pre-processing of the acquired data still in the area of the identification unit. Thus, in the context of this pre-processing, these data can be standardized for a simple processing later.

In an advantageous embodiment of the inventive device, the evaluation unit here can be, for instance, a PC workplace with a monitor and keyboard or a mobile hand device. Thus, by means of the keyboard, for instance, patient identification information can additionally be entered, ensuring an unequivocal allocation of the acquired objects to the patient.

In an especially useful and preferred configuration of the inventive device, the evaluation unit is connected with a touch screen to form a single unit that makes possible the processing of the scanned information in connection with an input by touching the display surface and/or by corresponding entry of operating and control commands.

The evaluation unit can be positioned inside the operating room, preferably in immediate proximity to the operating table and/or in an area of the operating room. Thus, the materials to be removed can be subjected to evaluation and further documentation immediately after, or even during, the operation to reach the acquisition and expanded documentation by a short route.

In a particularly advantageous embodiment, the evaluation unit is positioned outside the operating room. This has the advantage that the acquisition and documentation can be conducted in a non-sterile area and consequently, because of the decreased risk of contamination, by the support personnel, who are not required to wear protective clothing for hygienic reasons as required for an operating room. In addition, the evaluation unit is not required to be made of specialized, complex, and thus expensive sterilizable materials.

It is expected that the evaluation unit first receives the raw data and/or raw data sets from an identification unit and that the data are then entered and stored, for instance in a standard tabular calculation program, so that the data sets contain information from the group product name, article designation, lot number, usability/expiration date, series number, which are selectively arranged in the tabular fields. After the data distribution is complete, evaluation data can then be automatically generated. For instance, an inventory file or material flow information can be produced.

An inventory file, stored in the evaluation unit, thus contains for instance the number of objects that were provided and used or applied for the patient during the operation. The generated inventory file can then be compared with a previous one, which was produced at the start of the procedure. Depending on the queries used, information can be provided, for instance by an OR documentation list, on whether and/or how many objects were actually used during the procedure. In particular, this allows a determination of whether all instruments and other materials applied were listed in complete and updated manner at the end of the operation. This information is important in the patient's interest.

In a preferred embodiment, the evaluation unit is connected electronically, for instance via GPRS/WLAN, with the central database, preferably of the hospital, also known as hospital information system (HIS). The evaluation results generated in the evaluation unit can then be controlled, for instance regularly or depending on the situation, particularly after a procedure is completed, sent to the central database of the hospital and/or called up by it and stored in the computer of the central database and/or further processed.

Thanks to the data acquisition which is constantly possible, material flow information within the hospital can be called up at any time, communicated, and/or displayed.

Because decisive data on every object are regularly registered in the central computer database at the moment of its entry into the hospital's sterile storage system and also at the time of acquisition in the operating room, it is particularly possible to conduct a permanent balance sheet of the stored inventory by using an electronic quantity and value recording method.

Thus the respective current inventory level and changes in inventory, for instance, can be displayed at any time by means of a graph or inventory list. In addition it is also possible to automatically deduct the depleted and/or applied objects and to allocate them to certain usage categories such as individual operating rooms, in order finally to produce a corresponding patient-based cost record.

The inventive device regularly comprises a container with an opening pointed upward, a base surface, and an interior space into which the conveyed objects are introduced using gravitational force. The container here can be produced from various materials. It is especially effective to select materials in such a way that they are autoclavable, that is, capable of withstanding water pressure treatment under pressures up to about 134 degrees C. without damage. Autoclavability is particularly essential and therefore of great advantage for the inventive device if the container for instance should be contaminated with blood and/or germs. In this case autoclaving allows a reuse of the container and thus a greater lifetime for the receptacle altogether, while non-autoclavable containers must be removed expensively as special medical waste after every contamination with germs.

In an additional advantageous embodiment, the container can be slid with respect to the storage and/or work space, for instance on rollers, or for example it should be capable of pivoting or tipping by means, for instance, of a weighing frame, by about 10 to 15 degrees. Thus the container can be moved, for instance placed first on rollers, totally without problems to the utilization site and there can be brought into the particular operating or moving position by the user according to need or preference, without any problems, making comfortable and ergonomic operation possible. This ensures that the inventive device is always available at the desired location and thereby an efficient documentation of the objects can be achieved.

An additional advantageous embodiment of the inventive device consists in the fact that the interior space of the container comprises dividing walls and, depending on the number of dividing walls, the interior space is divided into at least two compartments. In this manner this container makes it possible that at least two categories of object can be sorted out and, in keeping with their sorting criteria, can be directed to one of the compartments. Thus just about all objects made of plastic, such as catheters and tubes, can be sorted, collected, and finally conveyed to the recycling facility. Objects thus removed and sorted into various compartments are documented, preferably selectively, so that a detailed evaluation becomes possible, for instance according to the size of the objects by category.

In another preferred embodiment an individual compartment can be configured so that an adaptation to various application requirements becomes possible on the basis of the prescribed objects used during the procedure. Thus, a compartment for the selective depositing of syringes can be configured with a particularly puncture-resistant wall to prevent possible injury during removal of the compartment. In addition, there can be differentiations in the capacity of compartments' volume or in the cross-sections of their openings.

This can be achieved either through differentiated combinations of modular components in the manufacturing process or through subsequent adjustments, or a combination of both. Thus, for instance, objects such as reusable surgical instruments can be collected by the sorting process so that they are subjected finally to a sterilization process in the course of instrument reconditioning.

In another practical embodiment, the containers and/or a compartment in the interior can be lined with a removable plastic sack. The sack is preferably provided with individualized markings that make documentation possible and/or improve logistics and/or removal.

In addition, a compartment an also be produced as a plastic sack or synthetic pouch and thus be used for objects that are not recyclable and are to be conveyed to refuse removal.

Another configuration of the inventive device concerns a container with an opening that faces upward and is provided with a lid to cover the opening. In any case, the opening of the container can be provided with a lid to cover the opening. It can also be arranged that several compartments each have a lid or cover and thus not all compartments require lids. This ensures a controlled insertion into the container or compartments, reducing erroneous deposits and thus improving the data quality of the documentation.

The one or more lids can be opened and closed manually. As a preferred alternative, lids can be opened and closed by electronic switches on the basis of a signal, received by the identification unit, for detecting objects to be removed. The control is configured in such a way that the container and/or compartment is closed after insertion of the object, thus preventing any unintended additional dropping or steering of a non-sorted object into the container and/or the compartment.

The inventive device is also preferably provided with a sorting device, which is positioned in the area of the container's opening and controlled as necessary, and which can use the information from the identification unit to control the device. Thus data are culled from the data carrier of the object by the identification unit, allowing in particular data on the specific sorting of an object. Thus the sorting destination is determined on the basis of such criteria as size, shape, material, type, and so on.

Then, in accordance with the sorting assignment, the object is mechanically transported away, for instance, and directed to a corresponding compartment. Thus the object itself transmits to the sorting device the data required for optimal removal. It is possible in this preferred manner to automatically document, sort, and unequivocally collect objects that resemble one another in the form and/or type of recycling they undergo, such as opened product packaging or surgical instruments.

Mechanical conveyance and/or sorting of objects can thus be effected by an alterable switch, for instance, which is mounted around a pivot axis and, by the position it assumes, determines into which compartment the sorted products are sent. Another possibility is a pivotable, sloping chute by which the sorted objects are selectively removed on the basis of gravity and finally fall into a compartment. In addition, an ejector or blowing nozzle can be provided for conveyance on a chute. This allows a very reliable selection of the objects, in particular with respect to logistics and removal, and consequently an informative documentation.

In another preferred embodiment of the inventive device, the device comprises a hand device that is connected by a connecting device, in particular with wireless support, with the identification unit. This makes it possible to read out the acquired, evaluated, or stored data, in particular, from the identification unit. In addition, object-related data that are necessary or helpful for the identification can be entered by the hand device and forwarded for instance, to the identification unit, and these data can be used in additional identification or evaluation.

It is also possible to connect a hand scanner for acquiring and reading from data carriers by means of the connection device. The connection between the hand device, hand scanner, and connection device should preferably be wireless. These embodiments are marked by the mobility of the hand devices or hand scanners, which allow for better data quality thanks to improved handling for the user.

According to an especially advantageous embodiment of the inventive device, it should be provided with a filling-level detection device in order to improve the additional logistical process of disposal with intermediate storage, transport, and final, especially thermal, disposal, on the basis of acquired filler-level data and its documentation.

The weight and/or volume of inserted objects is determined by the filler-level detection device. In addition the weight and volume of a container and/or compartment can be measured by means of a filler-level detection device upon insertion into the container and/or into a compartment. Also, depending on the case, the total weight and/or total volume of all inserted objects can be computed from these data. The measured weight and/or volume value can then be conveyed to a display unit. The filler level can thus be recognized and, for instance, stored and/or displayed, if and when the maximum filler volume of the container and/or compartment has been reached and consequently the container and/or compartment needs to be emptied or replaced.

Inserted refuse can be weighed, for instance, by a weighing platform that is positioned below the container and/or compartment and is equipped with a weight recorder/sensor to detect changes in weight. This configuration can be especially advantageously used when the refuse exceeds a drop height after it is inserted into the interior space of the container and/or compartment. In another advantageous embodiment, the weighing platform is constructed so that it comprises several force transducers corresponding to the number of compartments, each being positioned under one compartment. This has the advantage that the change in a compartment's weight can be individually measured and displayed, especially when an object is directed to this compartment.

Another preferred embodiment provides that the container and/or compartment has at least one distance sensor available for detecting volume. It is particularly advantageous if the distance sensor is positioned immediately below the predetermined filler height of the container and/or compartment, so that the filler height of the container and/or of a compartment is measurable with its help automatically and continuously, and also any overfilling of the container and/or compartment is reliably prevented. In addition, identified objects can be verified against stored object profiles by weighing them. This permits a clear increase in security.

Even without weighing or determining volume, information on the weight or volume of the identified objects can be determined by object profiles stored in the database and from that the filler status of the container is determined. Thus it is possible to reliably document which objects are present in the container, particularly a filled container, and which are jointly removed in a sack. The sacks removed from the container are preferably provided with individualized markers that make the additional documentation possible.

In another practical configuration of the invention, the identification unit is a component of a cap, particularly a ring-shaped one, that can be positioned so that it can be removed from and applied to a container. This cap is preferably in a single piece and self-supporting. Thus the ring opening of the cap continues into the opening of the container and thus allows a clear identification by means of the cap. With this inventive structure, the container can be emptied in especially simple and rapid manner by removing the cap. In addition the cap can also be mounted on other containers without problem and/or can be subjected to a sterilization process after acquisition of objects, thus increasing the operational readiness of the invention.

An additional especially advantageous embodiment of the inventive device concerns a video camera whose field of vision includes the area of the container's opening and which is capable of clearly identifying objects that are conducted to the area of the opening of the container and/or compartment, for instance on the basis of their formal properties. Thus it is also possible and advantageous to acquire and document objects which, for instance, are not equipped with a data carrier. In addition it is possible, nevertheless, to identify objects whose data carrier for instance has been damaged and which thus can no longer be scanned by a given reader head. The likelihood that an object equipped with a data carrier cannot be read is additionally reduced by this refinement, further improving the quality of the documentation.

DETAILED DESCRIPTION OF THE INVENTION

An exemplary embodiment of the inventive device and of the technical environment of the invention is now further described with reference to FIG. 1. The invention is not restricted to this illustrated embodiment.

Figure 1:
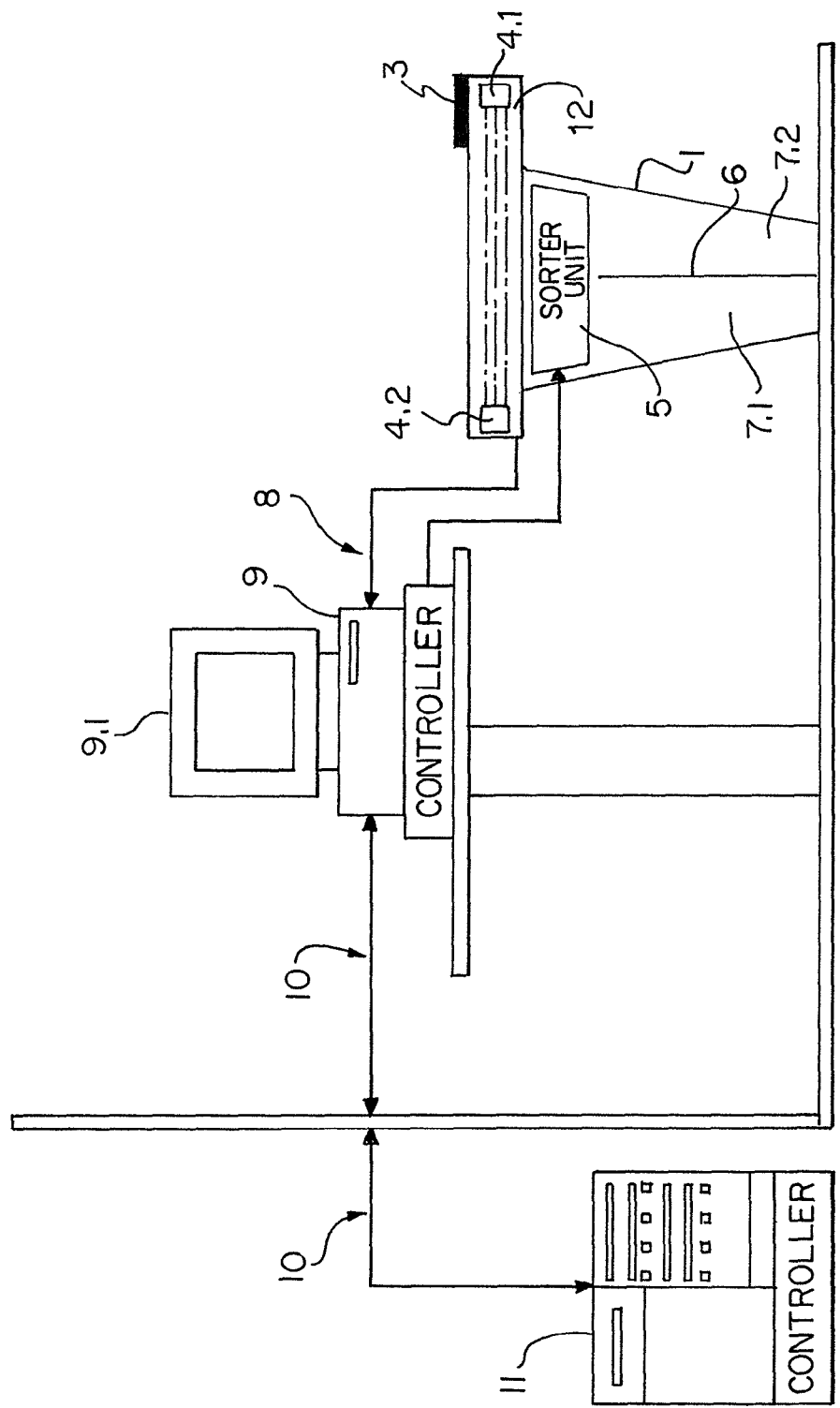
FIG. 1 shows an operating room including a device for receiving of disposable items.

Here FIG. 1 shows an operating room 20 whose sterile area is separated by a wall 25 from the non-sterile area 30. In addition, FIG. 1 shows a device, standing on the floor of the operating room, for receiving objects for an operation room 20 that are to be removed. The device shows and comprises a two-chamber container 1 with an identification unit 2 positioned in the area of the opening of the container 1 along with a sorting device 6. This device's positioning is selected below the identification unit 2.

Figure 3:
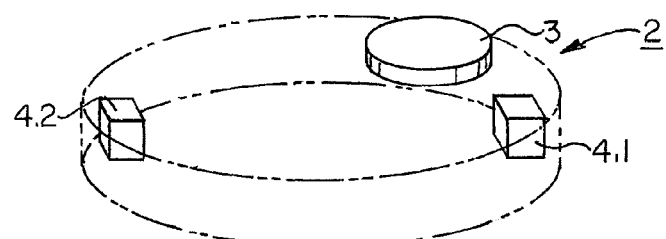
FIG. 3 shows one embodiment of an identification unit which comprises three reader heads.

The identification unit 2 is positioned on the upper edge of the container 1 and integrated into a removable ring-shaped cap 12, so that its opening continues into the opening of the container 1. As shown in FIG. 3, the identification unit 2 comprises a first reader head 3, a second 4.1, and a third reader head 4.2. They are configured for the detection of objects that are to be removed and for the reading of information from data carriers connected with the objects as soon as they are brought into their detection areas. The data carriers contain information that serves for individual identification and are applied on the respective object.

The reader heads 4.1 and 4.2 are positioned with respect to one another so that their detection areas overlap in FIG. 1 in a manner not shown in closer detail and cover the entire area of the opening of the container 1.

On the basis of this arrangement of two reader heads in facing position, it is guaranteed that if one reader head cannot acquire and read the data carrier, for instance if the data carrier is covered up, then at least the other reader head is capable of doing so.

The illustrated reader heads 3, 4.1, and 4.2 read the barcode and/or RFID identification data as a rule from data carriers that are brought into the range of their detection areas and are accordingly configured as barcode or RFID scanners.

Figure 2:
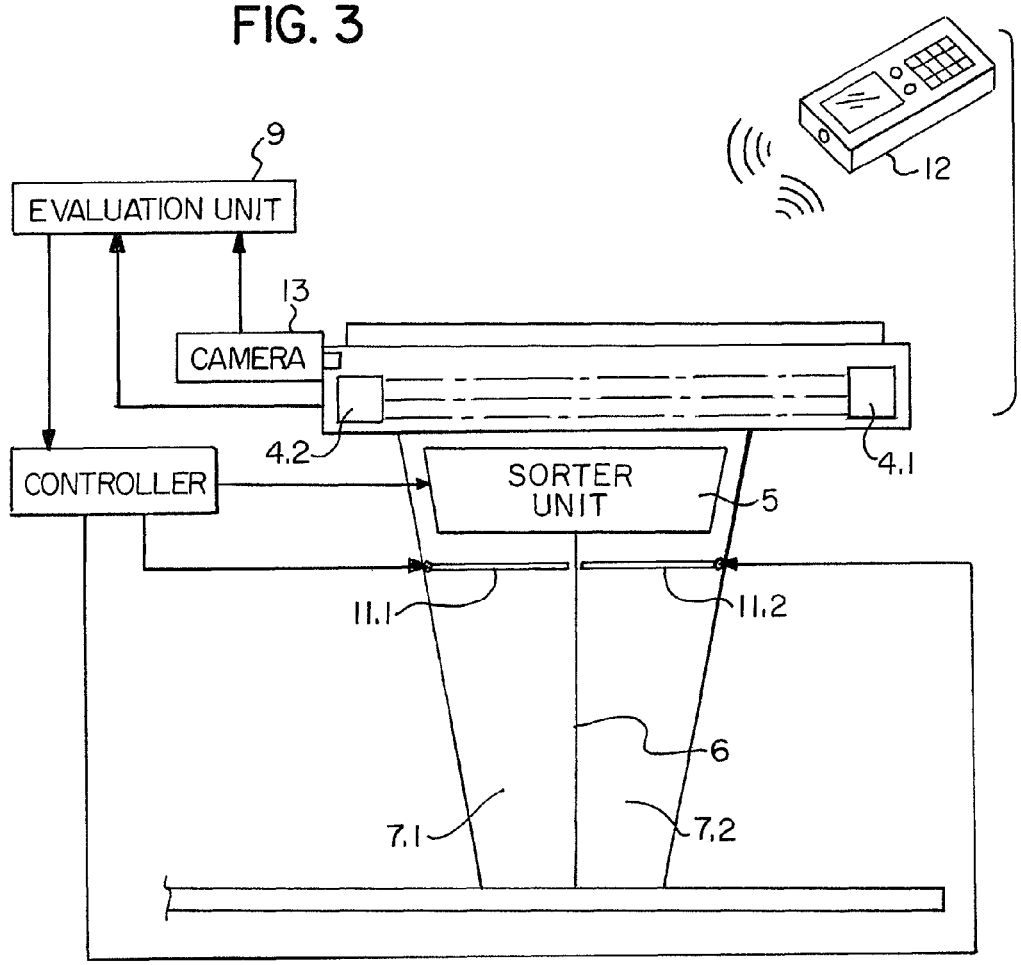
FIG. 2 shows details of a device for receiving of disposable items.

FIG. 2 shows that a video camera 13 is provided on the upper edge of the container 1 in order to acquire the area of the opening for data relating to the identify objects to be disposed of into the container 1. Such data include, for instance, the basis of the objects' formal properties. The video camera 13 then transmits the data to an evaluation unit 9.

In addition, FIG. 1 shows a two-chamber container that comprises an essentially trapezoidal-shaped longitudinal section. The interior of the container 1 is divided in its lower area into two compartments 7.1 and 7.2, separated from one another by a dividing wall 6 that extends from the floor of the container upward. The deposited objects are sorted with the help of a sorting unit 6. The first 7.1 and second 7.2 compartments serve to receive selectively sorted objects, which differ in their product characteristics, for instance their material and/or function. The separating wall 6 ensures that the objects sorted in the container according to differing product characteristics can no longer be mingled together.

Mounted downstream of the identification unit 2 is the sorting unit 5, which is positioned in the area of the opening but is smaller in dimension. The position of a conductor element determines in which compartment the sorted objects end up. The sorting of objects here can be done for instance by means of an angular profile alterable switch as conductor element, which is mounted to pivot around an axis. The sorting device 5 thus receives information that has been read out by the identification unit 2 from the data carriers of the objects and contains or admits indications on the sorting categories of an object. The object is then diverted and removed according to the sorting assignment.

The container 1 comprises two compartments 7.1 and 7.2, positioned side by side. The diverted objects, according to their sorting category, by which they are sorted, are fed toward the left into the first compartment 7.1 or toward the right into the second compartment 7.2. Each compartment 7.1 or 7.2 may have a lid 11.1 or 11.2 as shown in FIG. 2. The lids 11.1 and 11.2 can be connected to a controller such that they can be opened and closed by electronic switches on the basis of a signal, received by the identification unit 2, for detecting objects to be removed.

The identification unit 2 and the evaluation unit 9 are connected to one another by a communication link 8 for the exchange of data. The data transfer here can occur through a cable between the identification unit 2 and the evaluation unit 9 or through an IR connection or Bluetooth connection.

All of the data ascertained and read out by the identification unit 2 run together in the evaluation unit 9. The transmitted data are first stored, so that they can be read out again and further evaluated or processed.

Evaluation of the entered data can be processed, for instance on the basis of evaluation procedures that may require no additional particular input operations by the user. Thus, after arrival of the data, total information on the conveyed objects is for instance determined or objects are grouped and/or displayed in tables according to their sorting categories. It is possible to continually modify and document the displays on the basis of a running input of data.

Entered data can be displayed on the monitor 9.1 of the evaluation unit 9 as a raw data set and/or in their evaluated form.

The acquired, evaluated, or stored data can also be read out in a hand device 12, as shown in FIG. 2. The hand device 12 is connected by a connecting device, in particular with wireless support, with the identification unit 2. Object-related data can also be entered by the hand device 12 and forwarded to the identification unit 2.

The final step is the indication of what type of surgical instrument or which medical expendable material is primarily present. Other acquired data such as the date and time of the data acquisition can also be displayed as needed, of course.

These data can be supplemented on the evaluation unit 9 by manual and/or speech-activated input of additional data such as patient identification data or indications on the operating room 20. Thus, data acquired in the area of the identification unit 2 and stored in the evaluation unit 9 can be unequivocally associated with a patient and/or an operating room 20 from which they were obtained. This is particularly important when an evaluation unit 9 is associated with various operating rooms 20 and/or used in a number of procedures.

Data and evaluation results processed by the evaluation unit 9 are then made available on a central computer 11 of the hospital, which is installed in a non-sterile area 30 of the hospital. The communication line 10 between the evaluation unit 9 and the central computer 11 of the hospital is configured here as a fiberglass cable. The data transmission can also be processed here with link-up to the Internet as data transfer system. In this case an update of the company/software of the evaluation unit and/or of the identification unit can be conducted by the evaluation unit, so that the user can use the current software versions in each case. The care and expansion of the data acquisition and/or data evaluation possibility in the context of the existing hardware is thus simple, reasonable in price, and rapid.

Positioned on the central computer 11 of the hospital is a database in which, in addition to the acquired and/or supplemented data, additional data are stored and contained, by means of which, in particular, the material flow in an operating room 20 can be depicted.

With the arrival of an object in the hospital's sterile storage unit, various identifying data on each object are registered and filed in the database. This occurs either manually or semi- or completely automatically. Thus, from these data on registered objects an allocation data set can then be produced. This allocation data set allows, among other things, a later allocation of raw data and evaluation results for a particular operating room 20 or the identification of objects acquired by the inventive device that are to be disposed of on the basis of the read-out data from data carriers. On the basis of this documentation it is possible to depict the material flow within the hospital thanks to the ongoing use of objects, and to simplify the removal logistics, the utilization or removal of the object.

What is claimed is:

1. A device for receiving of disposable items for an operating room, comprising a container equipped with an opening, an identification unit positioned in close proximity to the opening, an evaluation unit communicating with the identification unit, and a central computer outside the operating room, the central computer comprising a central database and communicating with the evaluation unit;

wherein a continuing detection area is created by the identification unit that corresponds to perimeter of the opening, wherein objects equipped with one or more data carriers are processed by the identification unit when they are disposed into the container through the opening, and wherein additional data of a patient or operation room are supplemented by manual or speech-activated input on the evaluation unit;

wherein the central computer depicts material flow based on the central database, the additional supplemented data, and the one or more data acquired by the identification unit.

2. The device according to claim 1, wherein the identification unit is equipped with at least one reader head, which is capable of acquiring data carriers and reading out the data from the data carriers.

3. The device according to claim 2, wherein the at least one reader head is at least one of a barcode scanner and an RFID reader and can read data carriers that are configured as at least one of barcodes and RFID tags.

4. The device according to claim 1, wherein a reader head covers the opening of the container with its detection area in such a way that objects equipped with data carriers are acquired.

5. The device according to claim 4, wherein the reader head is at least one of a barcode scanner and an RFID reader and can read data carriers that are configured as at least one of barcodes and RFID tags.

6. The device according to claim 1, wherein the identification unit comprises two or more reader heads that are distanced and positioned from one another in such a way that the detection areas of the reader heads overlap.

7. The device according to claim 6, wherein at least one of the reader heads is at least one of a barcode scanner and an RFID reader and can read data carriers that are configured as at least one of barcodes and RFID tags.

8. The device according to claim 1, wherein the identification unit can be connected by a communication link with a remote evaluation unit outside of the operating room.

9. The device according to claim 1, wherein the device further comprises a hand device, the hand device wirelessly communicating with the evaluation unit, wherein the hand device acquires and reads data carriers that are connected with objects to be disposed of, enters additional supplemented data, or reads out acquired, evaluated or stored data.

10. The device according to claim 1, wherein the container is equipped with a filler level detection device which acquires the volume and/or weight of inserted objects and in particular, from this data, computes, emits, or stores in a storage device the total weight and/or total volume of all inserted objects.

11. The device according to claim 1, wherein an interior space of the container includes one or more dividing walls in such a way that the container is divided into individual compartments for receiving various objects.

12. The device according to claim 1, wherein the container comprises one or more lids to cover the opening of the container and/or the opening of one compartment,
wherein the one or more lids automatically open and close the container and/or compartment under control of the identification unit in response to the sorting category of the object to be disposed of 13. The device according to claim 1, wherein in the area of the opening a sorting device is positioned, which controlled by the identification unit, conducts an object that is to be disposed of to a compartment corresponding to its sorting category on the basis of acquired data.

14. The device according to claim 1, wherein a ring-shaped cap is provided on the container, where said cap contains the identification unit and can be positioned in the area of the opening of the container so that it can be removed and replaced.

15. The device according to claim 1, further comprising at least one video camera positioned in close proximity to the opening, the evaluation unit communicating with the at least one video camera;
wherein the at least one video camera is capable of clearly identifying objects that fall into its field of vision;
wherein a continuing detection area is created by the at least one video camera which field of vision includes the area of the opening; and
wherein the identity information of objects are processed by the at least one video camera when the objects are disposed into the container through the opening.

16. The device according to claim 15, wherein the additional data are supplemented by speech-activated input.

17. The device according to claim 15, wherein the container comprises one or more lids to cover the opening of the container and/or the opening of one compartment, wherein the one or more lids automatically open and close the container and/or compartment under control of the identification unit.

18. The device according to claim 15, wherein in the area of the opening a sorting device is positioned, which controlled by the identification unit, conducts an object that is to be disposed of to a compartment corresponding to its sorting category on the basis of acquired data.

19. The device according to claim 1, wherein the additional data are supplemented by speech-activated input.

* * * * *